United States Patent
Rodby et al.

(10) Patent No.: US 8,731,671 B2
(45) Date of Patent: May 20, 2014

(54) HEADER CONTACT FOR AN IMPLANTABLE DEVICE

(75) Inventors: Kevin P. Rodby, Shoreview, MN (US); David A. Chizek, Brooklyn Park, MN (US); Lawrence D. Swanson, White Bear Lake, MN (US); John M. Edgell, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 176 days.

(21) Appl. No.: 13/207,811

(22) Filed: Aug. 11, 2011

(65) Prior Publication Data

US 2012/0053663 A1 Mar. 1, 2012

Related U.S. Application Data

(60) Provisional application No. 61/376,783, filed on Aug. 25, 2010.

(51) Int. Cl.
*A61N 1/375* (2006.01)

(52) U.S. Cl.
USPC ............................... 607/37; 607/36; 439/843

(58) Field of Classification Search
USPC ....................................... 607/36, 37; 439/843
See application file for complete search history.

(56) References Cited

U.S. PATENT DOCUMENTS

| 4,002,400 | A | | 1/1977 | Evans |
| 5,730,628 | A | * | 3/1998 | Hawkins ....................... 439/843 |
| 5,766,042 | A | | 6/1998 | Ries et al. |
| 5,989,077 | A | | 11/1999 | Mast et al. |
| 2002/0107554 | A1 | * | 8/2002 | Biggs et al. ..................... 607/37 |
| 2006/0264122 | A1 | * | 11/2006 | Aman et al. .................. 439/843 |
| 2008/0248690 | A1 | | 10/2008 | Drew |

FOREIGN PATENT DOCUMENTS

WO WO-2012027125 A1 3/2012

OTHER PUBLICATIONS

"International Application Serial No. PCT/US2011/047393, International Search Report mailed Jan. 27, 2012", 3 pgs.
"International Application Serial No. PCT/US2011/047393, Written Opinion mailed Jan. 27, 2012", 7 pgs.
"International Application Serial No. PCT/US2011/047393, International Preliminary Report on Patentability mailed Mar. 7, 2013", 9 pgs.

* cited by examiner

*Primary Examiner* — Christopher D Koharski
*Assistant Examiner* — Michael Carey
(74) *Attorney, Agent, or Firm* — Schwegman, Lundberg & Woessner, P.A.

(57) ABSTRACT

An implantable medical device includes a housing, a header mounted to the housing, the header including a header body having a bore with an electrical contact located within the bore, wherein the electrical contact includes a plurality of contact points, wherein at least two of the contact points are longitudinally offset from each other along the bore.

20 Claims, 4 Drawing Sheets

HEADER CONTACT FOR AN IMPLANTABLE DEVICE

CROSS-REFERENCE TO RELATED APPLICATIONS

This application claims the benefit of U.S. Provisional Application No. 61/376,783, filed on Aug. 25, 2010, under 35 U.S.C. §119(e), which is incorporated herein by reference in its entirety.

BACKGROUND

Leads implanted in or about the heart have been used to reverse certain life threatening arrhythmia, or to stimulate contraction of the heart. Electrical energy is applied to the heart via electrodes on the leads to return the heart to normal rhythm.

A header on an implantable device is used to couple a conductor of the lead with circuitry within the implantable device. For instance, a contact in the header is used to electrically couple a cardiac stimulator system with the lead and electrode for making contact with a portion of the heart. U.S. Pat. No. 5,766,042 discusses a header with cylindrical multi-beam contacts.

It is desirable that the connection between the lead and the header is mechanically and electrically reliable.

OVERVIEW

The present inventors have recognized, among other things, a need for an implantable medical device that can include a housing, and a header mounted to the housing, the header including a header body having a bore with an electrical contact located within the bore, wherein the electrical contact includes a plurality of contact points, wherein at least two of the contact points are longitudinally offset from each other along the bore.

Example 1 can include subject matter that can include an implantable medical device, in which the implantable medical device can comprise: a housing; and a header mounted to the housing, the header including a header body having a bore with an electrical contact located within the bore, wherein the electrical contact includes a plurality of contact points, wherein at least two of the contact points are longitudinally offset from each other along the bore.

In Example 2, the subject matter of Example 1 can optionally comprise the electrical contact including a plurality of longitudinal leaf springs with a middle portion of each leaf spring bent inward to define a leaf spring contact point of each leaf spring, wherein at least two of the leaf springs include leaf spring contact points that are longitudinally offset from each other.

In Example 3, the subject matter of any of Examples 1-2 can optionally comprise the electrical contact being cylindrical.

In Example 4, the subject matter of any of Examples 1-3 can optionally comprise the electrical contact including a first end and a second end wherein a first end of each leaf spring is attached to a common structure of the first end and a second end of each leaf spring is attached to a common structure of the second end.

In Example 5, the subject matter of any of Examples 1-4 can optionally comprise the electrical contact being mounted within the bore with one of the first end or the second end rigidly fixed and the other of the first end or the second end movable longitudinally within the bore.

In Example 6, the subject matter of any of Example 1-5 can optionally comprise a lead including a terminal configured to be received within the header bore.

In Example 7, the subject matter of any of Examples 1-6 can optionally comprise the terminal including a metallic contact portion and an insulative polyurethane portion.

In Example 8, the subject matter of any of Examples 1-7 can optionally comprise the electrical contact including a cylindrical spring mounted to a contact housing wall in a winding configuration such that some contact portions of the cylindrical spring are located towards a front end of the bore and some contact portions of the cylindrical spring are located towards a back end of the bore.

In Example 9, the subject matter of any of Examples 1-8 can optionally comprise the winding configuration being a back-and-forth continuous S-shaped configuration.

In Example 10, the subject matter of any of Examples 1-9 can optionally comprise the electrical contact being formed of an MP35N alloy.

Example 11 can comprise, or can optionally be combined with the subject matter of any of Examples 1-10 to optionally comprise, a header for an implantable medical device comprising: a header body including one or more bores to receive a terminal of a lead; and an electrical contact located within the bore, the electrical contact including a cylindrically shaped body including a plurality of leaf springs extending longitudinally along the body, each of the leaf springs including a first end, a second end and a middle portion, wherein the middle portion of each leaf spring is bent inward to form a contact point and wherein at least two of the leaf springs include leaf spring contact points that are longitudinally offset from each other to form a longitudinally expanded spring contact zone.

In Example 12, the subject matter of any of Examples 1-11 can optionally comprise the electrical contact including a first end and a second end wherein a first end of each leaf spring is attached to a common structure of the first end and a second end of each leaf spring is attached to a common structure of the second end.

In Example 13, the subject matter of any of Examples 1-12 can optionally comprise the electrical contact being mounted within the bore with one of the first end or the second end rigidly fixed and the other of the first end or the second end movable longitudinally within the bore.

In Example 14, the subject matter of any of Examples 1-13 can optionally comprise the contact spring being formed of an MP35N alloy.

In Example 15, the subject matter of any of Examples 1-14 can optionally comprise the electrical contact being mounted within a metallic cylindrical housing.

In Example 16, the subject matter of any of Examples 1-15 can optionally comprise each contact point of adjacent leaf springs of the plurality of leaf springs being slightly moved from an adjacent leaf resulting in a sinuous contact point pattern.

Example 17 can comprise, or can optionally be combined with the subject matter of any of Examples 1-16 to comprise a method that can include: inserting a lead terminal into a bore of a header of an implantable device; the lead terminal contacting a first contact point of an electrical contact located within the header; and the lead terminal contacting a second contact point of the electrical contact after contacting the first contact point.

In Example 18, the subject matter of any of Examples 1-17 can optionally comprise contacting the first contact point including compressing a leaf spring.

In Example 19, the subject matter of any of Examples 1-18 can optionally comprise the lead terminal including a metallic contact portion and an insulative polyurethane portion.

In Example 20, the subject matter of any of Examples 1-19 can optionally comprise contacting the first contact point including compressing a cylindrical spring mounted to a contact housing wall in a winding configuration.

These examples can be combined in any permutation or combination. This overview is intended to provide an overview of subject matter of the present patent application. It is not intended to provide an exclusive or exhaustive explanation of the invention. The detailed description is included to provide further information about the present patent application.

DETAILED DESCRIPTION

Figure 1:
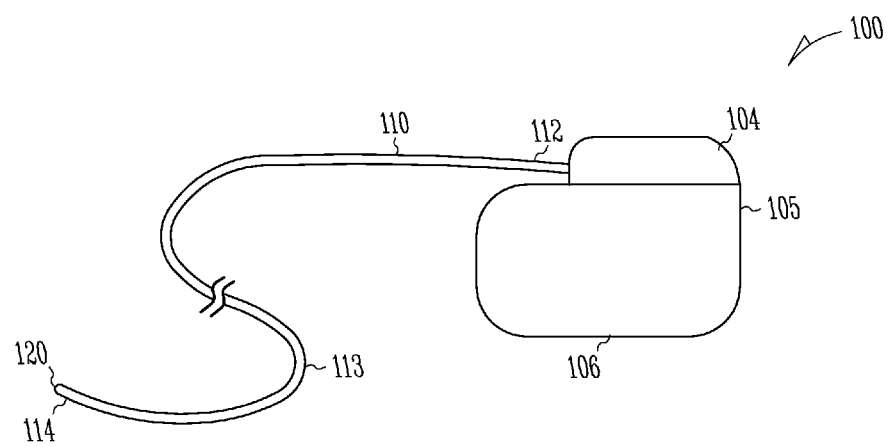
FIG. 1 shows a view of an implantable system according to at least one example.

FIG. 1 shows an implantable system 100, in accordance with one embodiment. The implantable system 100 includes a pulse generator 105 and at least one lead 110. The pulse generator 105 includes a housing 106 and a header 104 mounted to the housing 106. The pulse generator 105 is generally implanted into a subcutaneous pocket made in the wall of the chest. Alternatively, the pulse generator 105 is placed in a subcutaneous pocket made in the abdomen, or in other locations. Pulse generator 105 can include a power supply such as a battery, a capacitor, and other components housed in the housing 106. The implantable device can include microprocessors to provide processing, evaluation, and to determine and deliver electrical shocks and pulses of different energy levels and timing for defibrillation, cardioversion, and pacing to a heart in response to cardiac arrhythmia including fibrillation, tachycardia, heart failure, and bradycardia.

The lead 110 includes a lead body 113 having a proximal end 112, where the lead is coupled at the header 104 of the pulse generator 105, as further discussed below. The lead 110 extends to a distal end 114, which is coupled with a portion of a heart, when implanted. The distal end 114 of the lead 110 includes at least one electrode 120 which electrically couples the lead 110 with a heart. At least one electrical conductor is disposed within the lead 110 and extends from the proximal end 112 to the electrode 120. The electrical conductor carries electrical currents and signals between the pulse generator 105 and the electrode 120.

In other embodiments, system 100 is suitable for use with implantable electrical stimulators, such as, but not limited to, pulse generators, neuro-stimulators, skeletal stimulators, central nervous system stimulators, or stimulators for the treatment of pain.

Figure 2:
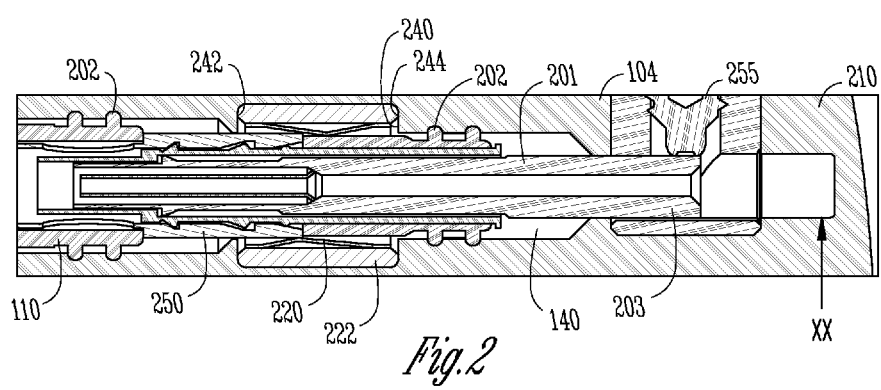
FIG. 2 shows a cross-section side view of a header, in accordance with one example.

FIG. 2 shows a cross-section side view of the header 104, in accordance with one example. The header 104 includes one or more bores 140 that are configured to receive a lead terminal 201 of the lead 110. In this example, the lead terminal 201 includes a proximal tip contact 203, a terminal ring contact 250 and one or more sealing rings 202 which help seal the bore 140 against body fluids. The terminal ring contact 250 is typically made of stainless steel and the sealing rings 202 and other insulative portions of terminal 201 are formed of polyurethane. The terminal ring contact 250 is coupled via a conductor to at least one electrode disposed on the lead 110.

The header 104 generally includes a header body 210 having the bore 140 formed therein and one or more electrical contacts 220 located within the bore 140 to electrically contact the corresponding contact 250 of the lead 110. The electrical contact 220 is mounted within a cylindrical, metallic contact housing 222 and is electrically connected to the electronics in the pulse generator. The contact 220 and the housing 222 are positioned in the header bore in an annular gap 240 molded into the header body. A first edge wall 242 and a second edge wall 244 of annular gap 240 constrain the contact 220 and the housing 222 within the bore 140.

The bore 140 can be molded within the body 210 and is sized to receive the terminal 201. In some examples, the bore 140 can include a series of decreasing diameter sections defining a series of steps, with one or more contacts located within each step. Likewise, the terminal 201 can include a stepped design with a series of decreasing diameter portions with one or more contacts on each section. Furthermore, in some embodiments, the device can include an optional set-screw 255 to help hold the lead terminal 201 in place within the header 104. Other embodiments omit the set-screw. In some examples, two or more contacts 220 are located within the bore 140. Other examples can include fewer or more contacts.

Figure 3:
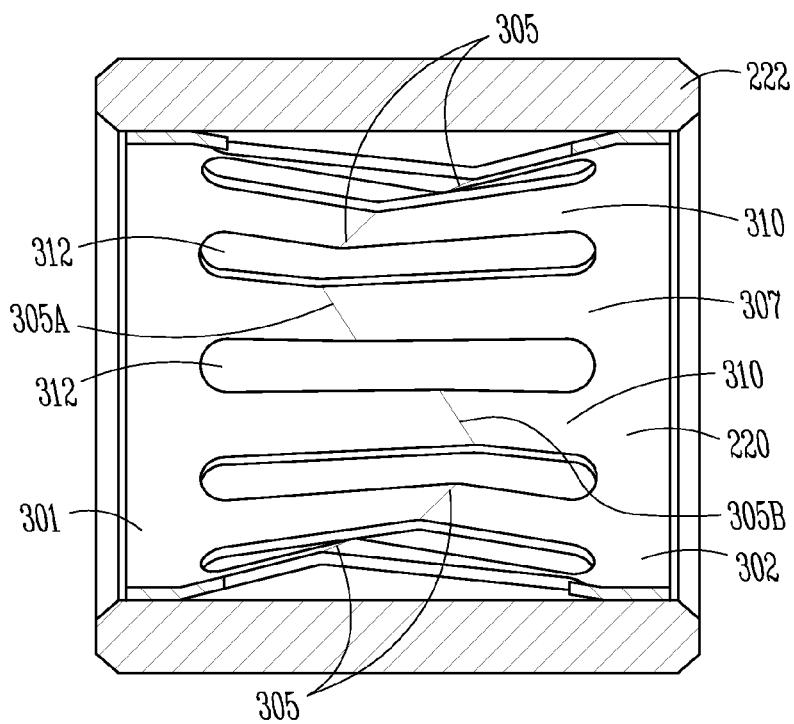
FIG. 3 shows a side view of an electrical contact for a header, in accordance with one example.
Figure 4:
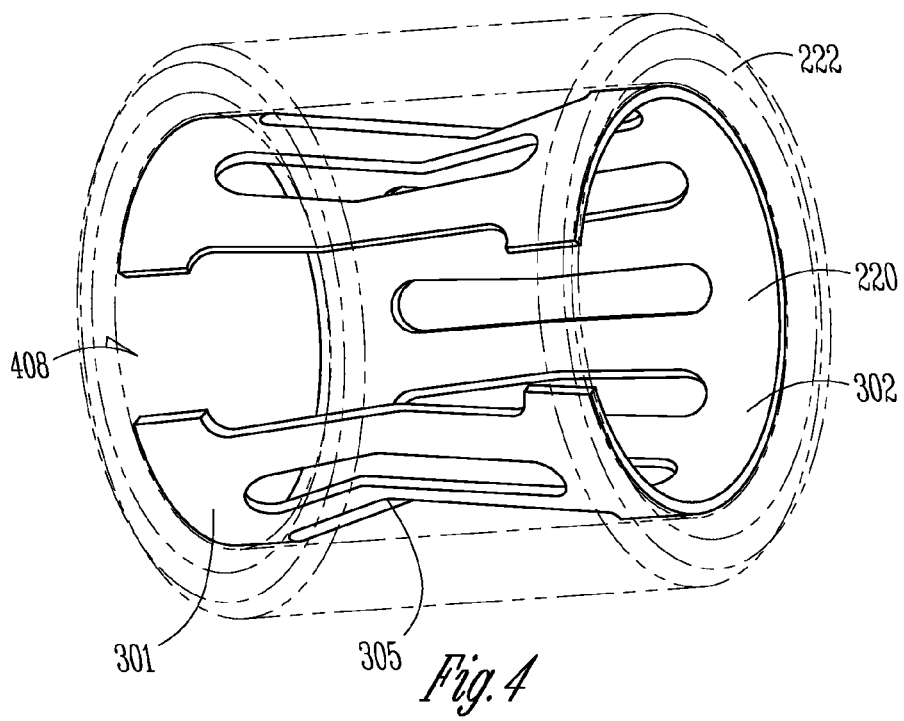
FIG. 4 shows a perspective view of the electrical contact of FIG. 3.
Figure 5:
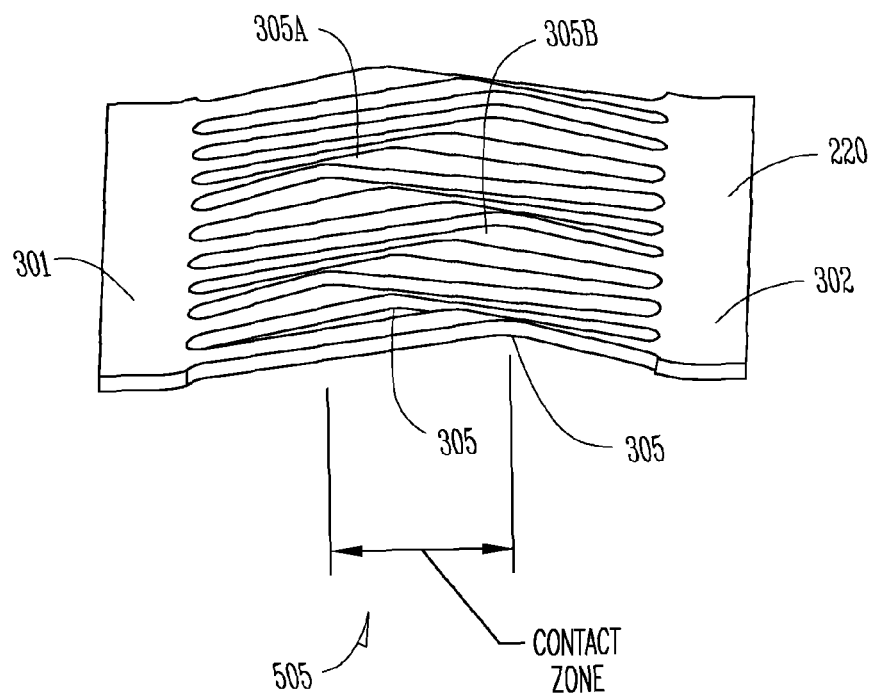
FIG. 5 shows a view of the electrical contact of FIGS. 3 and 4 in flattened form, according to one example.

FIGS. 3, 4, and 5 show further details of the electrical contact 220, in accordance with one example. FIG. 3 shows a side view of the electrical contact 220 within contact housing 222, FIG. 4 shows a perspective view of the electrical contact 220 within the contact housing 222, and FIG. 5 shows a view of the electrical contact 220 in flattened form.

The electrical contact 220 includes a main body 307 formed into a cylindrical shape with a number of leaf springs 310 separated by slots 312. The present example includes ten leaf springs 310. Other examples can utilize more or fewer leaf springs as desired. The contact 220 includes a first end portion 301 and a second end portion 302 with the leaf springs 310 extending longitudinally along the cylindrical body from one end portion 301 to the other end portion 302. In certain examples, each end portion 301 and 302 is a solid structure such that each of the leaf springs 310 is fixed to a common structure at each respective end 301 and 302. In other words, neither end of any leaf spring 310 is free-floating in this example. This structure can help prevent any damage to the sealing rings and other polyurethane portions of the lead terminal since there are no exposed edges to catch on the lead terminal.

The leaf springs 310 have strength to provide sufficient force against lead terminal ring contact 250 (FIG. 2) to provide sufficient electrical and mechanical contact between the lead and the header. The leaf springs 310 are sloped with a crease or bent section in the middle portion of the leaf forming a peak or projection that forms a contact point 305 for each leaf 310. These contact points 305 are radially deflected when a lead is inserted through the contact 220.

In certain examples, a contact point 305 of one of the leaf springs 310 is offset longitudinally from a contact point 305 of a different leaf 310. For example, contact point 305A is closer to first end 301 and contact point 305B is closer to second end 302 of the contact 220. This longitudinal offset of contact points of two or more of the leaf springs 310 defines a longitudinally expanded contact zone 505 for the contact 220. Thus, when a lead terminal is inserted into the header bore, the lead terminal first contacts contact point 305A, for example, and then second and third contact points of different leaf springs 310 and finally contact point 305B.

In this example, each contact point 305 of adjacent leaf springs 310 is slightly moved from an adjacent leaf resulting in a sinuous pattern (best seen in FIG. 5). In other examples, at least two of the leaf springs 310 include leaf spring contact points 305 that are longitudinally offset from each other.

Typical contact zones on previous header contacts are in a single radial location on the lead connector. This limits the electrical contact zone for the lead connector to the contact of the header, and can create the possibility of a no-connect of the contact to the ring terminal of the lead in a condition of under-insertion of the lead. The present contact 220 design increases the contact zone 505 of the contact. This reduces errors caused by slight under-insertion of the lead into the header bore. Referring to FIG. 2, point XX represents the point of full insertion of the lead terminal 201. Here, the lead terminal 201 is shown as being under-inserted. However, because of the enlarged contact zone of the present contact 220, the contact 220 still makes electrical contact with terminal ring contact 250. Thus, the present design results in a robust, clean electrical connection even if there is an under-insertion of the lead terminal.

Also, typical single-zone contacts cause an insertion force spike when all the spring contacts come into contact with the lead at the same time. Staggering the contact points expands the contact zone 505 longitudinally along the bore and thereby spread out the insertion force resulting in a lower peak insertion force.

For example, as the leaf springs 310 are first moved by the lead terminal 201 an initial peak force arises on the lead terminal, then as the lead terminal enters further, the given leaf applies a drag force to the lead terminal. In the present example, the initial peak forces applied by the various leaf springs 310 are staggered along the contact zone 505. This initial peak force is followed by the same drag force as in past contacts. However, by staggering the initial peak force, a contact having the same initial peak force as in past contacts will have a higher final spring compression force on the lead and potentially more stable contact resistance. In other words, the present contact 220 can have a smaller inner diameter (defined by the contact points 305) than previous connectors, which results in a higher final spring compression force. However, because the contact points 305 are spread along contact zone 505, the initial peak force can be the same or less than past contacts.

In this example, the contact 220 is curled into the cylindrical housing 222 that can be made of 316L stainless steel. In certain examples, the contact 220 is curled in such a way that it does not quite form a complete enclosure inside the housing 222, thus leaving a small gap 408. The spring contact 220 can be spot welded to the housing 222 on one end of the contact, for example. Since the weld only constrains the contact 220 axially in one spot, the spring expands its axial length longitudinally along the housing 222 as it deflects upon lead insertion. In some examples, the spring can also expand radially into the gap 408. In other examples, more than one weld can be used to secure the contact 220 in the housing 222. In certain examples, no welds are used and the contact 220 is merely positioned within the housing 222 and held by frictional forces. In certain examples, the contact 220 and the housing 222 can be press-fit into the header 104 (FIG. 2) with either end facing the bore header.

In one example, the spring contact 220 includes an inner diameter of about 0.0988 inches to about 0.1014 inches. This is the size for a 0.106 lead pin, such as for an IS-1 lead terminal diameter. Other embodiments utilize almost any diameter, according to lead terminal size.

In one example, the contact 220 is formed using a punch and die-forming manufacturing process. For example contact 220 can be punched from a sheet of MP35N material. The contact 220 blank is punched with the slotted features first and then formed with a die to create the offset raised contact points 305 in the leaf springs. The contact 220 blank is then rolled into a cylindrical cage form and assembled into the housing 222.

Figure 6:
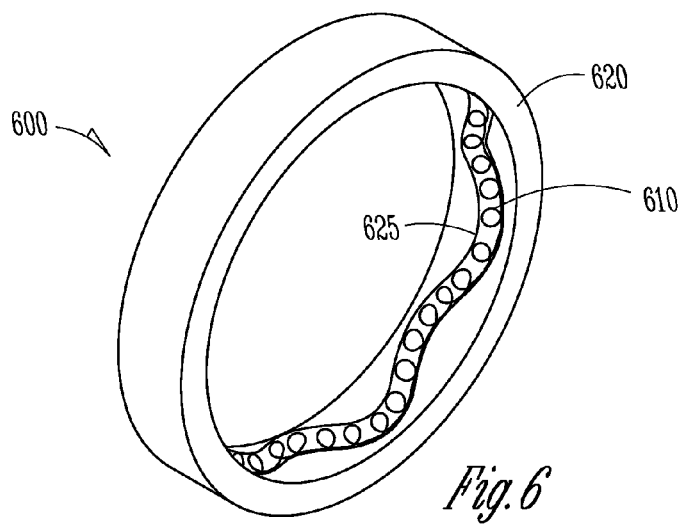
FIG. 6 shows a perspective view of an electrical contact for a header, in accordance with one example.

FIG. 6 shows a perspective view of an electrical contact 600 for a header, in accordance with one example. In this example, the contact 600 includes a tightly wound cylindrical spring 610 mounted to a groove 625 formed in the inner wall of a metallic contact housing 620 in a winding configuration such that some contact portions of the cylindrical spring 610 are located towards a front end of the contact 600 and some contact portions of the cylindrical spring 610 are located towards a back end of the contact 600. In this example, the winding configuration of groove 625 is a back-and-forth continuous S-shaped configuration.

Figure 7:
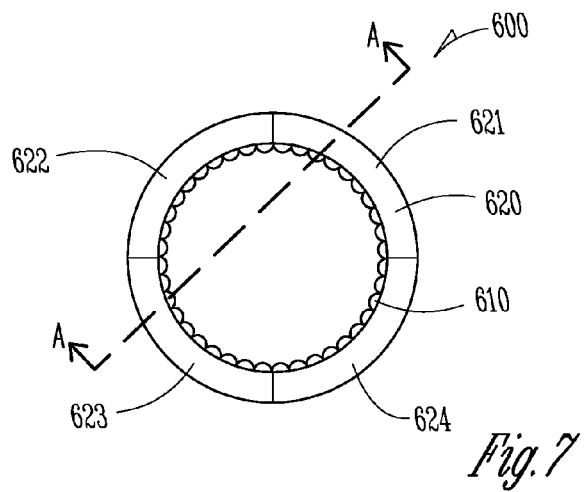
FIG. 7 shows a front view of the electrical contact of FIG. 6, in accordance with one example.

FIG. 7 shows a front view of the electrical contact 600, in accordance with one example. The housing 620 can include four assembly sections 621, 622, 623, and 624. Assembly sections 621, 622, 623, and 624 are formed as quarter-circles, in this example. This allows the groove 625 to be more easily machined within the housing 620 since each section 621-624 can be machined separately. After each assembly section 621-624 is formed and the grooves are separately made in each assembly section, the assembly sections 621-624 are welded together with each separate groove mating with an adjacent groove to form the single sinuous groove 625.

Figure 8:
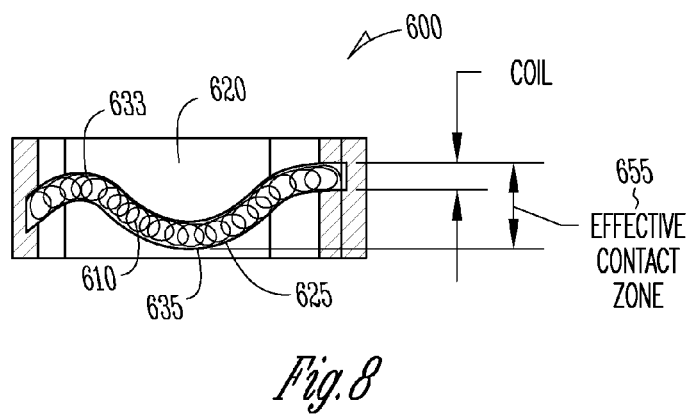
FIG. 8 shows a section view of the electrical contact of FIG. 7, in accordance with one example.

FIG. 8 shows a section view of the electrical contact 600, in accordance with one example. The sinuous pattern of the cylindrical spring 610 mounted within groove 625 of housing 620 results in an expanded contact zone 655 since contact portion 633 of the cylindrical spring 610 is located towards one end of the contact 600 and contact portion 635 of the cylindrical spring 610 are located towards the other end of the contact 600. As discussed above, typical contact zones on previous header contacts are in a single radial location on the lead connector. This limits the electrical contact zone for the lead connector to the contact of the header, and can create the possibility of a no-connect of the header contact to the ring terminal of the lead in a condition of under-insertion of the lead. The present contact 600 design increases the contact zone 655 of the contact. This reduces errors caused by slight under-insertion of the lead into the header bore.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An implantable medical device comprising:
    a housing; and
    a header mounted to the housing, the header including a header body having a bore with one or more electrical contacts located within the bore, wherein at least one of the one or more electrical contacts includes a plurality of contact points integrally formed as part of the at least one electrical contact, wherein at least two of the contact points are longitudinally offset from each other along the bore, such that a first contact point is closer to a front opening of the bore than a second contact point of the electrical contact.

2. The implantable medical device of claim 1, wherein the electrical contact includes a plurality of longitudinal leaf springs with a middle portion of each leaf spring bent inward to define a leaf spring contact point of each leaf spring, wherein at least two of the leaf springs include leaf spring contact points that are longitudinally offset from each other.

3. The implantable medical device of claim 2, wherein the electrical contact is cylindrical.

4. The implantable medical device of claim 2, wherein the electrical contact includes a first end and a second end wherein a first end of each leaf spring is attached to a common structure of the first end and a second end of each leaf spring is attached to a common structure of the second end.

5. The implantable medical device of claim 4, wherein the electrical contact is mounted within the bore with one of the first end or the second end rigidly fixed and the other of the first end or the second end movable longitudinally within the bore.

6. The implantable medical device of claim 2 further including a lead including a terminal configured to be received within the header bore.

7. The inrplantabie medical device of claim 6, wherein the terminal includes a metallic contact portion and an insulative polyurethane portion.

8. The implantable medical device of claim , wherein the electrical contact includes a cylindrical spring mounted to a contact housing wall in a winding configuration such that some contact portions of the cylindrical spring are located towards a front end of the bore and some contact portions of the cylindrical spring are located towards a back end of the bore.

9. The implantable medical device of claim 8, wherein the winding configuration is a back-and-forth continuous S-shaped configuration.

10. The implantable medical device of claim 1, wherein the electrical contact is formed of an MP35N alloy.

11. A header for an implantable medical device comprising:
    a header body including one or more bores to receive a terminal of a lead; and
    an electrical contact located within the bore, the electrical contact including a cylindrically shaped body including a plurality of leaf springs extending longitudinally along the body, each of the leaf springs including a first end, a second end and a middle portion, wherein the middle portion of each leaf spring is bent inward to form a contact point and wherein at least two of the leaf springs located within a single, discrete, integral electrical contact include leaf spring contact points that are longitudinally offset from each other, such that a first contact point is closer to a front opening of the bore than a second contact point of the electrical contact so as to form a longitudinally expanded spring contact zone.

12. The header of claim 11, wherein the electrical contact includes a first end and a second end wherein a first end of each leaf spring is attached to a common structure of the first end and a second end of each leaf spring is attached to a common structure of the second end.

13. The header of claim 11, wherein the electrical contact is mounted within the bore with one of the first end or the second end rigidly fixed and the other of the first end or the second end movable longitudinally within the bore.

14. The header of claim 11, wherein the contact spring is formed of an MP35N alloy.

15. The header of claim 11, wherein the electrical contact is mounted within a metallic cylindrical housing.

16. The header of claim 11, wherein each contact point of adjacent leaf springs of the plurality of leaf springs is slightly moved from an adjacent leaf resulting in a sinuous contact point pattern.

17. A method comprising:
   inserting a lead terminal into a bore of a header of an implantable device;
   the lead terminal contacting a first contact point of a discrete electrical contact located within the header; and
   the lead terminal contacting a second contact point of the discrete electrical contact after contacting the first contact point, wherein the first contact point and the second contact point are configured such that the first contact point is closer to a front opening of the bore than the second contact point of the electrical contact.

18. The method of claim 17, wherein contacting the first contact point includes compressing a leaf spring.

19. The method of claim 17, wherein the lead terminal includes a metallic contact portion and an insulative polyurethane portion.

20. The method of claim 17, contacting the first contact point includes compressing a cylindrical spring mounted to a contact housing wall in a winding configuration.

* * * * *